(12) United States Patent
Daum et al.

(10) Patent No.: US 7,050,854 B2
(45) Date of Patent: May 23, 2006

(54) CALIBRATION OF ADAPTIVE-RATE PACING USING INTRINSIC CHRONOTROPIC RESPONSE

(75) Inventors: Douglas R. Daum, Oakdale, MN (US); Quan Ni, Shoreview, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 712 days.

(21) Appl. No.: 10/178,277

(22) Filed: Jun. 24, 2002

(65) Prior Publication Data

US 2004/0015195 A1 Jan. 22, 2004

(51) Int. Cl.
*A61N 1/365* (2006.01)

(52) U.S. Cl. .......................................... 607/17; 607/19
(58) Field of Classification Search ................... 607/19, 607/17–18, 25, 28
See application file for complete search history.

(56) References Cited

U.S. PATENT DOCUMENTS

| | | | | |
|---|---|---|---|---|
| 5,292,340 | A | * | 3/1994 | Crosby et al. ................. 607/17 |
| 5,350,409 | A | * | 9/1994 | Stoop et al. .................... 607/17 |
| 5,391,189 | A | * | 2/1995 | van Krieken et al. .......... 607/17 |
| 5,423,870 | A | * | 6/1995 | Olive et al. ..................... 607/18 |
| 5,792,198 | A | * | 8/1998 | Nappholz ...................... 607/18 |
| 6,055,454 | A | | 4/2000 | Heemels |

OTHER PUBLICATIONS

Journal of Electrophysiology, vol. 3, No. 3, 1989: *A Mathematical Model of the Cardiac Chronotropic Response to Exercise*, Bruce L. Wilkoff, M.D., Joseph Corey, and Gordon Balckburn, Ph.D., pp. 176-180.

Clinical Cardiac Pacing, Ellenbogen, Kay, Wilkoff, 1995, Chapter 26: *Cardiac Chronotropic Responsiveness*, Bruce L. Wilkoff, pp. 432-446.

* cited by examiner

*Primary Examiner*—George Manuel
*Assistant Examiner*—Nicole R. Kramer
(74) *Attorney, Agent, or Firm*—Schwegman, Lundberg, Woessner & Kluth, P.A.

(57) ABSTRACT

Calibration of adaptive-rate pacing by a cardiac rhythm management system using an intrinsic chronotropic response. The cardiac rhythm management system may include an adaptive-rate pacing device. The adaptive-rate pacing device may include an adaptive-rate sensor module for measuring an activity level of the individual. A monitor module may be coupled to the adaptive-rate sensor module, the monitor module monitoring an intrinsic chronotropic response. A calculator module may be coupled to the monitor module, the calculator module calculating a calibrated parameter for the adaptive-rate pacing device based on the intrinsic chronotropic response. An adjuster module may be coupled to the calculator module, wherein the adjuster module adjusts the adaptive-rate pacing device based on the calibrated parameter. The parameters of the adaptive-rate pacing device adjusted by the adjuster module may include a sensor rate target, a maximum sensor rate, and a response factor.

6 Claims, 9 Drawing Sheets

CALIBRATION OF ADAPTIVE-RATE PACING USING INTRINSIC CHRONOTROPIC RESPONSE

TECHNICAL FIELD

This invention relates to a cardiac rhythm management system. In addition, the invention relates to calibration of adaptive-rate pacing by a cardiac rhythm management system using an intrinsic chronotropic response.

BACKGROUND

A healthy individual's heart rate (HR) increases intrinsically as the individual's physical activity or emotional level increases. This intrinsic chronotropic response to increased activity or work load allows the individual's heart to pump oxygen-rich blood more quickly throughout the body. As used herein, the phrase "chronotropic response" means a change in the rate of heart contraction. The phrase "intrinsic heart rate" means the inherent rate of heart contraction without artificial pacing. For example, the intrinsic heart rate may be the rate set by the sinoatrial or atrioventricular nodes.

Activity and work load are used interchangeably herein to represent an individual's current state of exertion, ranging from a resting state to maximal exertion. An individual's heart rate will increase with increased activity or work load until the heart rate reaches a maximum heart rate. This maximum heart rate can be approximated using the following Equation 1 to calculate a maximal predicted heart rate ($PHR_{max}$).

$$PHR_{max} = 220 - \text{age} \quad (1)$$

As shown by Equation 1, the $PHR_{max}$ decreases with age.

The difference between an individual's $PHR_{max}$ and resting heart rate ($HR_{resting}$), or the individual's heart rate during relaxation, is termed the individual's heart rate reserve (HRR) and can be calculated as shown in Equation 2.

$$HRR = PHR_{max} - HR_{resting} \quad (2)$$

The individual's HRR is a measure of the individual's capacity to increase heart rate and can be expressed in terms of % HRR, calculated for any given level of activity $HR_{stage}$ as shown in Equation 3.

$$\% \ HRR = \frac{HR_{stage} - HR_{rest}}{PHR_{max} - HR_{rest}} \times 100\% \quad (3)$$

Another relevant measurement of an individual's activity level is the metabolic equivalent (MET), which measures the oxygen uptake of the individual. A MET is equal on average to 3.5 mL of $O_2$/kg per minute. By measuring an individual's oxygen consumption and converting the oxygen consumption into METs, the individual's exercise capacity can be measured. An individual's metabolic reserve (MR) is a measure of the individual's total metabolic capacity. An individual's MR can be calculated by taking the difference between an individual's maximal and minimal MET values, as shown in Equation 4.

$$MR = MET_{maximal} - MET_{resting} \quad (4)$$

A percentage MR for any given stage of metabolic activity $METS_{stage}$ can be calculated as shown in Equation 5.

$$\% \ MR = \frac{METS_{stage} - METS_{rest}}{METS_{maxmal} - METS_{rest}} \times 100\% \quad (5)$$

Figure 1:
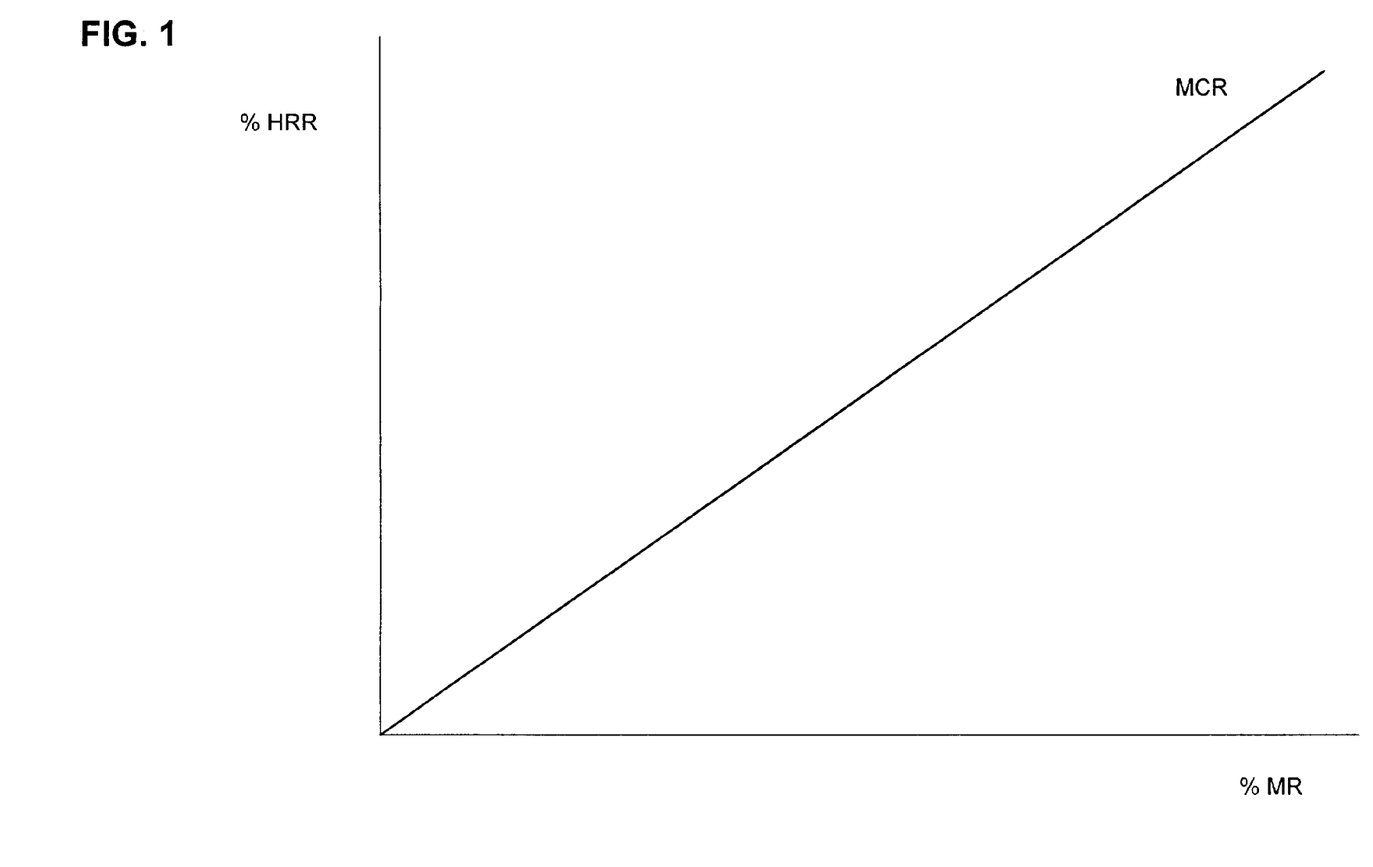
FIG. 1 is a graphical representation of a percentage metabolic reserve plotted versus a percentage heart rate reserve illustrating a metabolic-chronotropic relation.

A linear relationship between % HRR and % MR has been identified and is illustrated in FIG. 1. In FIG. 1, the % HRR is plotted against % MR for a healthy individual. As illustrated, a healthy individual exhibits a linear rise in the percentage of HRR equal to that of the percentage of MR. In other words, as an individual's percentage of metabolic reserve utilized increases, the individual's percentage of heart rate reserve utilized increases proportionally. This relationship is mathematically represented for any given activity level by Equation 6 and is shown in simplified form in Equation 7.

$$HR_{stage} = \frac{(220 - \text{age} - HR_{rest}) \times (METS_{stage} - 1)}{METS_{maxmal} - 1} + HR_{rest} \quad (6)$$

$$HR_{stage} = (HRR \times \% \ MR) + HR_{rest} \quad (7)$$

The relationship between % HRR and % MR, as illustrated in FIG. 1 and Equations 6 and 7, is termed the metabolic-chronotropic relation (MCR). The MCR generally illustrates that as a healthy individual's physical activity or work load increases, the individual's intrinsic heart rate and associated cardiac output increases proportionally.

However, in some individuals with heart abnormalities, such as those suffering from sick sinus syndrome, an increase in activity or work load does not always evoke an associated proportional increase in heart rate. Studies on individuals suffering from sick sinus syndrome have shown that, although some individuals exhibit normal intrinsic chronotropic responses to increased activity at certain times, these individuals are intermittently chronotropic incompetent, resulting in situations in which the individual's heart rate increases little or not at all for an increase in work load.

A cardiac rhythm management (CRM) system is a common solution for problems associated with a heart's inherent electrical functions. Therefore, for individuals suffering from heart abnormalities such as sick sinus syndrome, a CRM system including adaptive-rate pacing may be used to artificially increase the individual's heart rate during increased activity and chronotropic incompetent periods, thereby providing increased hemodynamic benefits for these individuals.

The fundamental components of a CRM system include a CRM device, such as a cardiac pacing device or a cardiac resynchronization device, which includes a pulse generator for creating electrical impulses to stimulate the heart. Also included are one or more electrodes for delivering the electrical impulses and sensing the heart's intrinsic electrical activity.

A CRM system may further provide adaptive-rate pacing by including an adaptive-rate pacing device with one or more adaptive-rate sensors. Adaptive-rate pacing utilizes the one or more adaptive-rate sensors to sense an increase in activity and artificially increase heart rate during the increased activity. Adaptive-rate pacing is premised on the metabolic-chronotropic relation, as illustrated in FIG. 1 and described above, in that adaptive-rate pacing assumes that an increase in activity is proportional to an increase in heart rate. Therefore, during adaptive-rate pacing, the one or more adaptive-rate sensors are used to measure an individual's increased activity or work load, and based on the measurements, an appropriate heart rate for the given activity is approximated.

Presently, there are three major types of commercial adaptive-rate sensors available, including activity sensors, minute ventilation sensors, and QT interval sensors. All three types of sensors use different physiological criteria to measure changes in activity or work load and therefore an increased need for cardiac output. When an adaptive-rate pacing device determines that an individual has increased his or her work load, the adaptive-rate pacing device increases the frequency at which electrical impulses are communicated to the individual's heart, thereby increasing the individual's heart rate and cardiac output.

Figure 2:
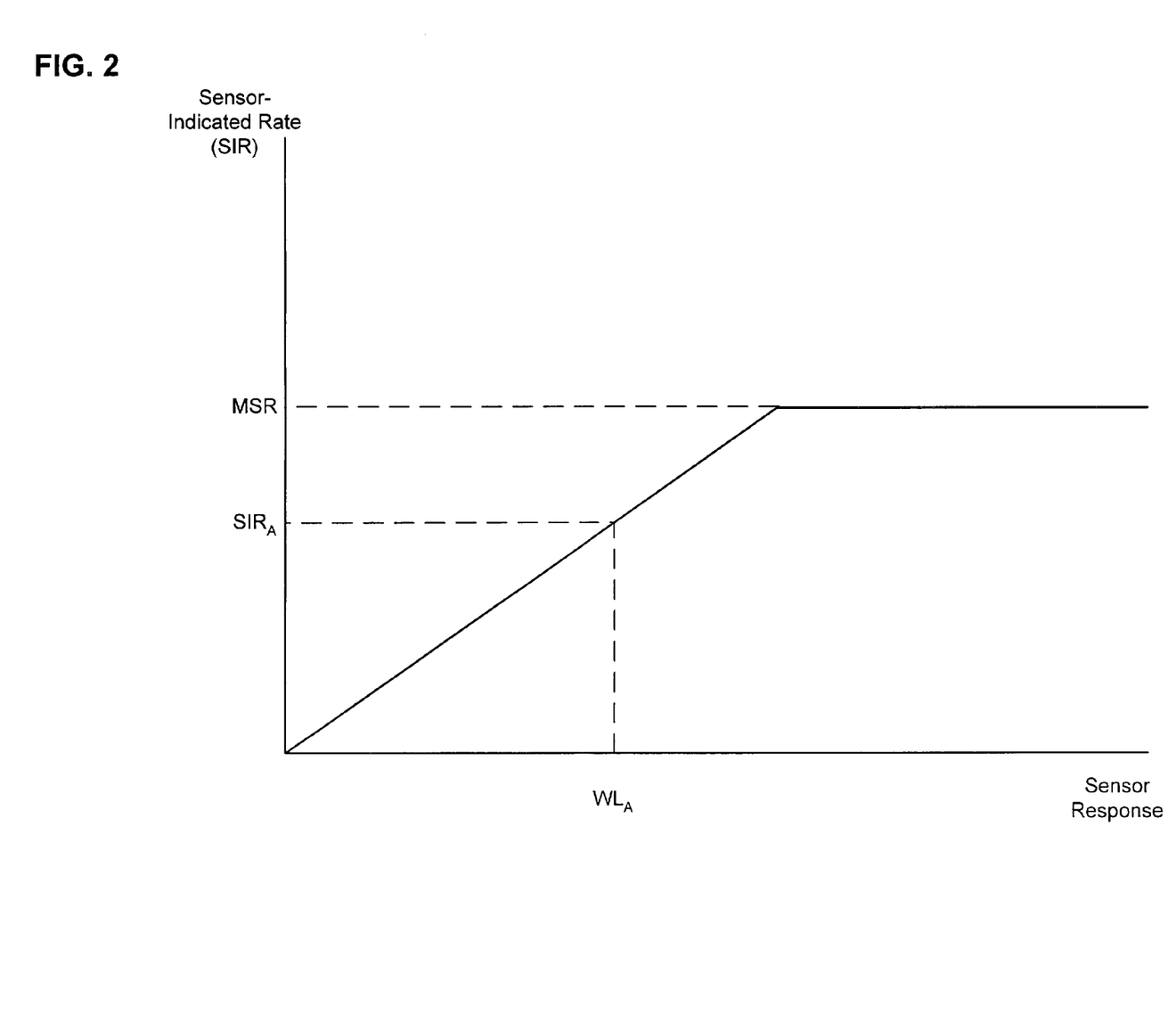
FIG. 2 is a graphical representation of a sensor response plotted versus a sensor-indicated rate illustrating a response of a typical adaptive-rate pacing device.

Illustrated in FIG. 2 is a second graph whereon a sensor-indicated rate (SIR) is plotted versus a sensor response. The SIR is the rate at which an adaptive-rate pacing device causes electrical impulses to be communicated to the heart and can range from zero (i.e. no pacing is provided) to a maximum sensor rate (MSR), which, for example, may be set at an individual's maximal predicted heart rate (see Equation 1). A sensor response is a signal communicated by the adaptive-rate sensor to the adaptive-rate pacing device, the signal being proportional to an increase in an individual's activity or work load.

The line provided in FIG. 2 illustrates the linear relationship between the sensor response and the SIR. For example, for a sensor response of a measured work load $WL_A$, the adaptive-rate pacing device will provide a SIR of $SIR_A$. A SIR for any given sensor response can be calculated using Equation 8.

$$\text{Sensor-Indicated Rate} = \text{Sensor Response} \times \text{Response Factor} \tag{8}$$

The response factor (RF) is a constant used to relate the sensor response of the adaptive-rate sensor to the SIR provided by the adaptive-rate pacing device. An increase in the RF will increase the SIR for a given sensor response. Conversely, a decrease in the RF will decrease the SIR for a given sensor response. This increase or decrease in the sensor-indicated rate translates into an increase or decrease in the pacing of the heart during chronotropic incompetence for a given level of activity.

Therefore, an adaptive-rate sensor can approximate a heart rate for a given level of activity by measuring the work load, provide a sensor response proportionate to the measured work load, and correlate the sensor response to a SIR by multiplying the sensor response by the response factor, as shown by Equation 8. The response factor determines how an adaptive-rate sensor responds to a given work load and therefore dictates the slope of the line shown in FIG. 2.

Figure 3:
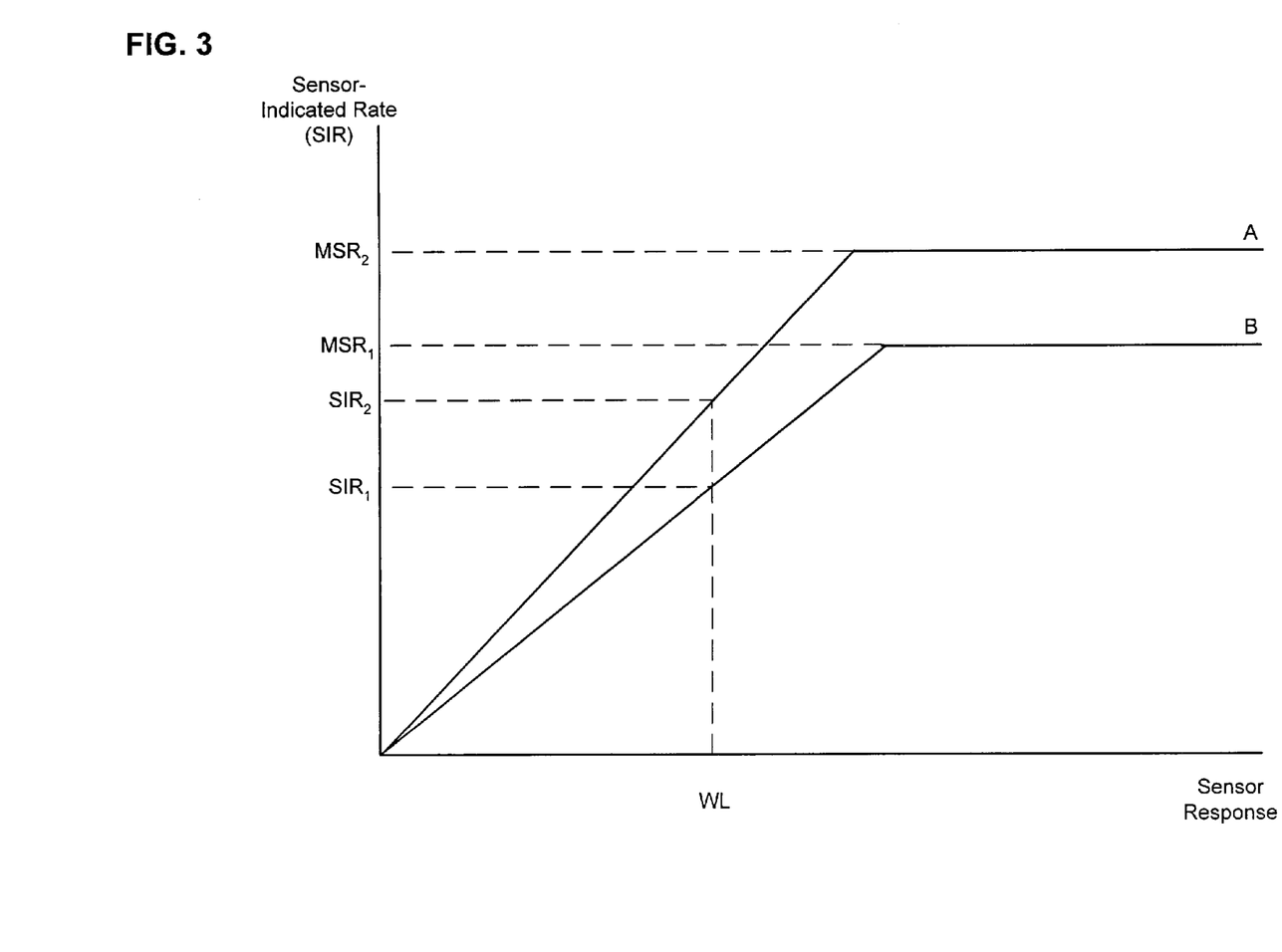
FIG. 3 is a graphical representation of a sensor response plotted versus a sensor-indicated rate illustrating responses for two typical adaptive-rate pacing devices that have been calibrated differently.

In FIG. 3, a graph similar to that shown in FIG. 2 illustrates two responses for two adaptive-rate pacing devices A and B that have been calibrated differently. As shown, a response factor for the adaptive-rate pacing device A is greater than a response factor for the adaptive-rate pacing device B. Because the response factor for pacing device A is greater than the response factor for pacing device B, the slope of line A is steeper than the slope of line B. Therefore, for a given work load and associated sensor response, such as $WL_1$, the sensor-indicated rate, e.g., $SIR_2$, for the adaptive-rate sensor A is greater than the sensor-indicated rate, e.g., $SIR_1$, for the adaptive-rate sensor B. The two sensor-indicated rates $SIR_1$ and $SIR_2$ differ because the response factors for the two adaptive-rate pacing devices A and B are different. In addition, a maximum sensor rate $MSR_2$ for the adaptive-rate pacing device A is configured to be greater than a maximum sensor rate $MSR_1$ for the adaptive-rate pacing device B.

Adaptive-rate pacing must be customized for each individual. An adaptive-rate pacing device is typically calibrated by a caregiver. Such variables as maximum sensor rate, response factor, and sensor rate target (described below) are typically configured using physiological data collected from the individual as well as one or more equations of general applicability. For example, a caregiver may use Equation 1 to set the MSR and Equation 6 to approximate an individual's heart rate at a given work load in an attempt to define an appropriate RF.

The practitioner may also attempt to optimize calibration by setting a sensor rate target (SRT). The SRT is an approximation of the individual's daily achieved maximum heart rate. The SRT is typically set using subjective data provided by the individual. For example, the SRT may be set using the individual's desired target heart rate during exercise. The SRT is used in conjunction with an average daily maximum paced heart rate ($\overline{MPHR}$) calculated by the CRM system. The $\overline{MPHR}$ is calculated by storing a maximum paced heart rate for each day for an individual over a specific time period. The daily maximum paced heart rates are then averaged to calculate the $\overline{MPHR}$. Then, based on the SRT and $\overline{MPHR}$, the adaptive-rate pacing device is calibrated using Equations 9 and 10 below.

$$\text{If } \overline{MPHR} > SRT, \text{ then } \downarrow RF \tag{9}$$

$$\text{If } \overline{MPHR} < SRT, \text{ then } \uparrow RF \tag{10}$$

As illustrated by Equation 9, if the $\overline{MPHR}$ is greater than the SRT, the RF is decreased to better approximate daily activity. Conversely, if the $\overline{MPHR}$ is less than the SRT, then the RF is increased.

Calibration of a CRM system, and particularly adaptive-rate pacing, as illustrated above, involves clinical experimentation as well as complex calculations. The calibration can take valuable time to perform and may encourage practitioners to take short-cuts in the calibration process. In addition, the complexity of the calibrations can cause mistakes to be made. As illustrated by the responses A and B shown in FIG. 3, the calibration of an adaptive-rate pacing device can have a significant effect on how an adaptive-rate pacing device responds to a given activity or work load. This can lead to episodes of hemodynamic deficiency, wherein an individual may become fatigued while performing at a certain work load because the individual's heart rate does not represent the typical chronotropic response for the given work load. Further, calibration of the CRM system may not adequately account for progressive changes in an individual's needs subsequent to calibration.

Therefore, calibration of an adaptive-rate pacing device remains a challenging task. The methods are complex, subjective, and do not automatically adapt to account for changes in an individual's cardiac output needs. In addition, there is the possibility that calibration will be improperly performed.

SUMMARY

Generally, the present invention relates to a cardiac rhythm management system and, more particularly, to calibration of adaptive-rate pacing by a cardiac rhythm management system using chronotropic response.

In one aspect, the invention relates to an adaptive-rate pacing device including an adaptive-rate sensor module coupled to a heart of an individual and an adaptive-rate sensor, wherein the adaptive-rate sensor measures an activity level of the individual and communicates a signal proportional to the activity level to the adaptive-rate sensor module, a monitor module coupled to the adaptive-rate sensor module, wherein the monitor module monitors an intrinsic chronotropic response, a calculator module coupled to the monitor module, wherein the calculator module calculates a calibrated parameter for the adaptive-rate pacing device based on the intrinsic chronotropic response, and an adjuster module coupled to the calculator module, wherein the adjuster module adjusts the adaptive-rate pacing device based on the calibrated parameter.

In another aspect, the invention relates to a cardiac rhythm management system including a cardiac rhythm management device coupled to an individual's heart, and an adaptive-rate pacing device coupled to the cardiac rhythm management device, wherein the adaptive-rate pacing device automatically calibrates at least one parameter of the adaptive-rate pacing device using an intrinsic chronotropic response of the individual.

In yet another aspect, the invention relates to a method for automatic calibration of an adaptive-rate pacing device, wherein the adaptive-rate pacing device is part of a cardiac rhythm management system, the method including steps of: monitoring a plurality of daily maximum intrinsic heart rates; processing the plurality of daily maximum intrinsic heart rates to calculate a calibrated parameter; and recalibrating a parameter associated with the adaptive-rate pacing device.

In another aspect, the invention relates to a method for automatically calibrating adaptive-rate pacing provided by a cardiac rhythm management system, the method including steps of: monitoring a plurality of daily maximum intrinsic heart rates; calculating an average maximum intrinsic heart rate from the plurality of daily maximum intrinsic heart rates; comparing the average maximum intrinsic heart rate to a sensor rate target; and increasing the sensor rate target if the average maximum intrinsic heart rate is greater than the sensor rate target.

In another aspect, the invention relates to a method for automatically calibrating adaptive-rate pacing provided by a cardiac rhythm management system, the method including steps of: monitoring a plurality of daily maximum intrinsic heart rates and associated sensor-indicated rates; calculating an average difference from a difference between each of the plurality of daily maximum intrinsic heart rates and associated sensor-indicated rates; comparing the average difference to a constant; and increasing incrementally a response factor if the average difference is greater than the constant.

In yet another aspect, the invention relates to a method for automatically calibrating adaptive-rate pacing provided by a cardiac rhythm management system, the method including steps of: monitoring a plurality of daily maximum intrinsic heart rates and associated sensor response; cross-checking each of the plurality of daily maximum intrinsic heart rates by comparing each of the plurality of daily maximum intrinsic heart rates to each associated sensor response; calculating an average maximum intrinsic heart rate from the plurality of daily maximum intrinsic heart rates; comparing the average maximum intrinsic heart rate to a maximum sensor rate; and increasing the maximum sensor rate if the average maximum intrinsic heart rate is greater than the maximum sensor rate.

The above summary of the present invention is not intended to describe each disclosed embodiment or every implementation of the present invention. The figures and the detailed description which follow more particularly exemplify these embodiments.

DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention relates to cardiac rhythm management (CRM) systems. In particular, the present invention is directed to calibration of adaptive-rate pacing by a CRM system using an intrinsic chronotropic response. While the present invention is not so limited, an appreciation of various aspects of the invention will be gained through a discussion of the examples provided below.

Generally, the devices and methods described below are premised on the fact that individuals suffering from heart abnormalities, such as sick sinus syndrome, are often only intermittently chronotropic incompetent. These individuals may exhibit periods during which their hearts respond to increased activity or work load in chronotropic competent manner, and other periods in which their hearts do not respond in a chronotropic competent manner.

Figure 4:
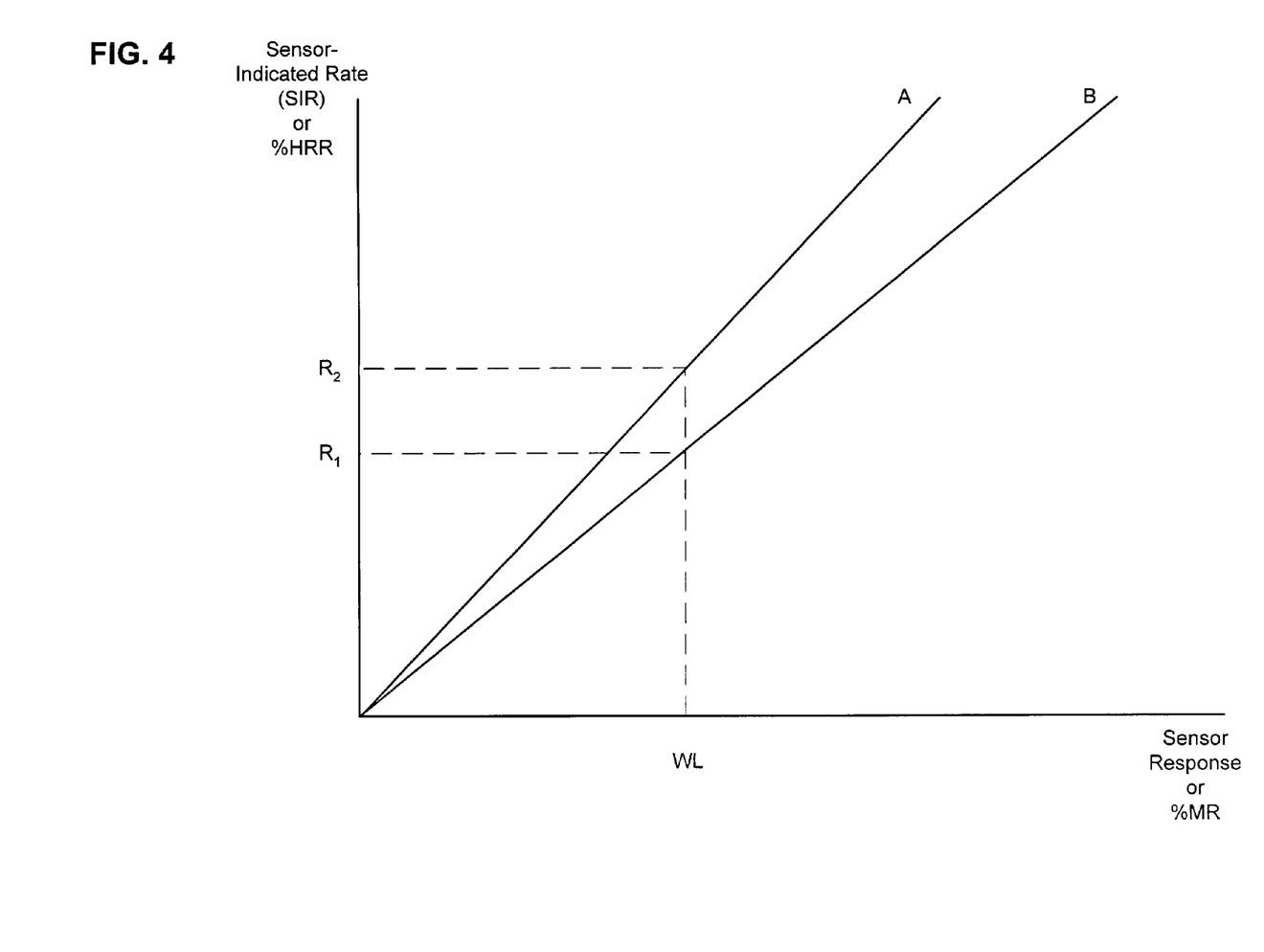
FIG. 4 is a graphical representation of a sensor response and a percentage metabolic reserve plotted versus a sensor-indicated rate and a percentage heart rate reserve illustrating a metabolic-chronotropic relation A and an adaptive-rate pacing device response B.

For example, in FIG. 4, a percentage metabolic reserve is plotted against a percentage heart rate reserve, and an individual's metabolic-chronotropic relation during an individual's chronotropic-competent period is shown as line A. As also shown in FIG. 4, a sensor response is plotted against a sensor-indicated rate, and an adaptive-rate pacing device output is shown as line B. As shown, for any given activity level or work load, e.g. WL, the individual's chronotropic response, e.g. $R_2$, is greater than the adaptive-rate sensor-indicated response, e.g. $R_1$. Therefore, because the individual exhibits chronotropic competent response that is higher than that of the adaptive-rate pacing device, the individual will not be paced during this period of chronotropic competency. It is only when the line A representing the individual's chronotropic response falls below that of the line B that the individual is paced using adaptive-rate pacing.

A primary goal of adaptive-rate pacing is to best approximate the intrinsic chronotropic response to increased activity or work load. Therefore, the devices and methods described herein utilize information collected during periods in which the individual is chronotropic competent to automatically calibrate adaptive-rate pacing to best approximate chronotropic response when the individual is chronotropic incompetent and adaptive-rate pacing is necessary.

I. Example Cardiac Rhythm Management System

Figure 5:
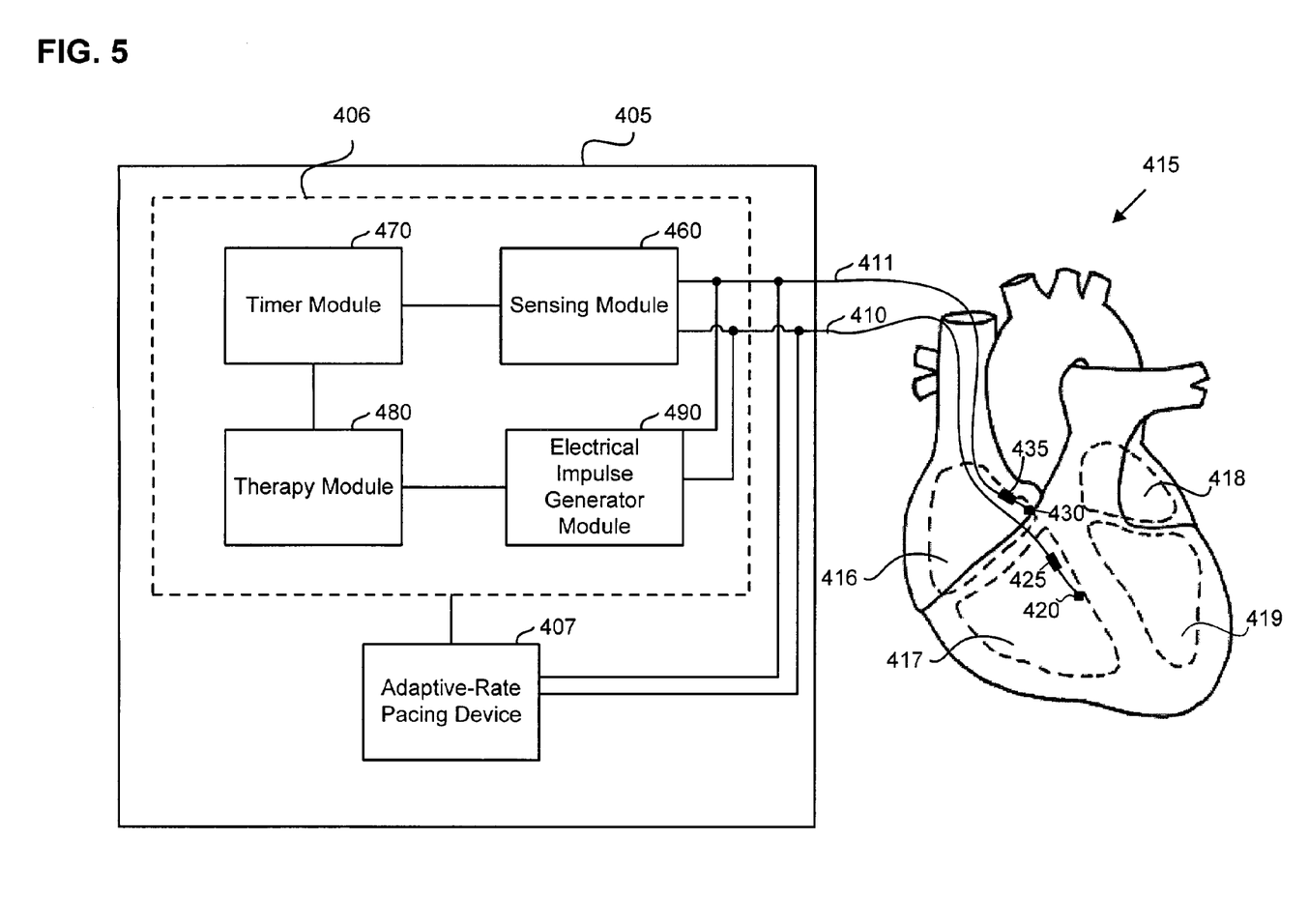
FIG. 5 illustrates a cardiac rhythm management system made in accordance with an example embodiment of the present invention.

An example embodiment of a CRM system 405 is illustrated in FIG. 5. The CRM system 405 includes a CRM device 406 coupled to an adaptive-rate pacing device 407. The CRM device 406 and the adaptive-rate pacing device 407 may be implemented as a single unit or may be implemented as individual units. In addition, both the CRM device 406 and the adaptive-rate pacing device 407 may be implanted into an individual.

Both devices 406 and 407 are coupled to a heart 415. The heart 415 includes a right atrium and ventricle 416 and 417 and a left atrium and ventricle 418 and 419. The devices 406 and 407 are coupled to the heart 415 via one or more leads 410 and 411. The leads 410 and 411 are introduced into the heart 415 via known techniques. The lead 411 is shown positioned in the right atrium 416, and the lead 410 is shown positioned in the right ventricle 417. Other positions are also possible, and more or few leads may also be used.

The leads 410 and 411 include tip electrodes 420 and 430 and ring electrodes 425 and 435. Other known types of electrodes may also be used. Each electrode is "associated" with the particular heart chamber, e.g., right and left ventricles 417 and 419, by inserting it into that heart chamber, or by inserting it into a portion of the heart's vascular that is close to that heart chamber, or by epicardially placing the electrode outside that heart chamber, or by any other technique of configuring and situating an electrode for sensing signals and/or providing therapy with respect to that heart chamber.

The CRM device 406 generally functions to monitor the activity of the heart 415 and provide pacing therapy when appropriate. The CRM device 406 may comprise several modules, including, but not limited to, a sensing module 460, a timer module 470, a therapy module 480, and an electrical impulse generator module 490. The sensing module 460 is coupled to the heart 415 via the leads 410 and 411 and monitors the electrical activity of the heart 415. The sensing module 460 may perform multiple functions, such as, for example, detecting individual heart contractions.

The timer module 470 is coupled to the sensing module 460. The timer module 470 performs general timing functions, such as timing the period between heart contractions. The therapy module 480 is coupled to the timer module 470. The therapy module 480 provides specific therapeutic modalities associated with a mode in which the CRM device 406 is functioning. For example, if the device 406 is performing as a pacing device, the device 406 would include the modalities associated with a typical pacemaker. The electrical impulse generator module 490 is coupled to the therapy module 480. The electrical impulse generator module 490 is controlled by the therapy module 480 and generates electrical impulses that are communicated to the heart 415 via the leads 410 and 411 to induce contraction of the heart 415.

Figure 6:
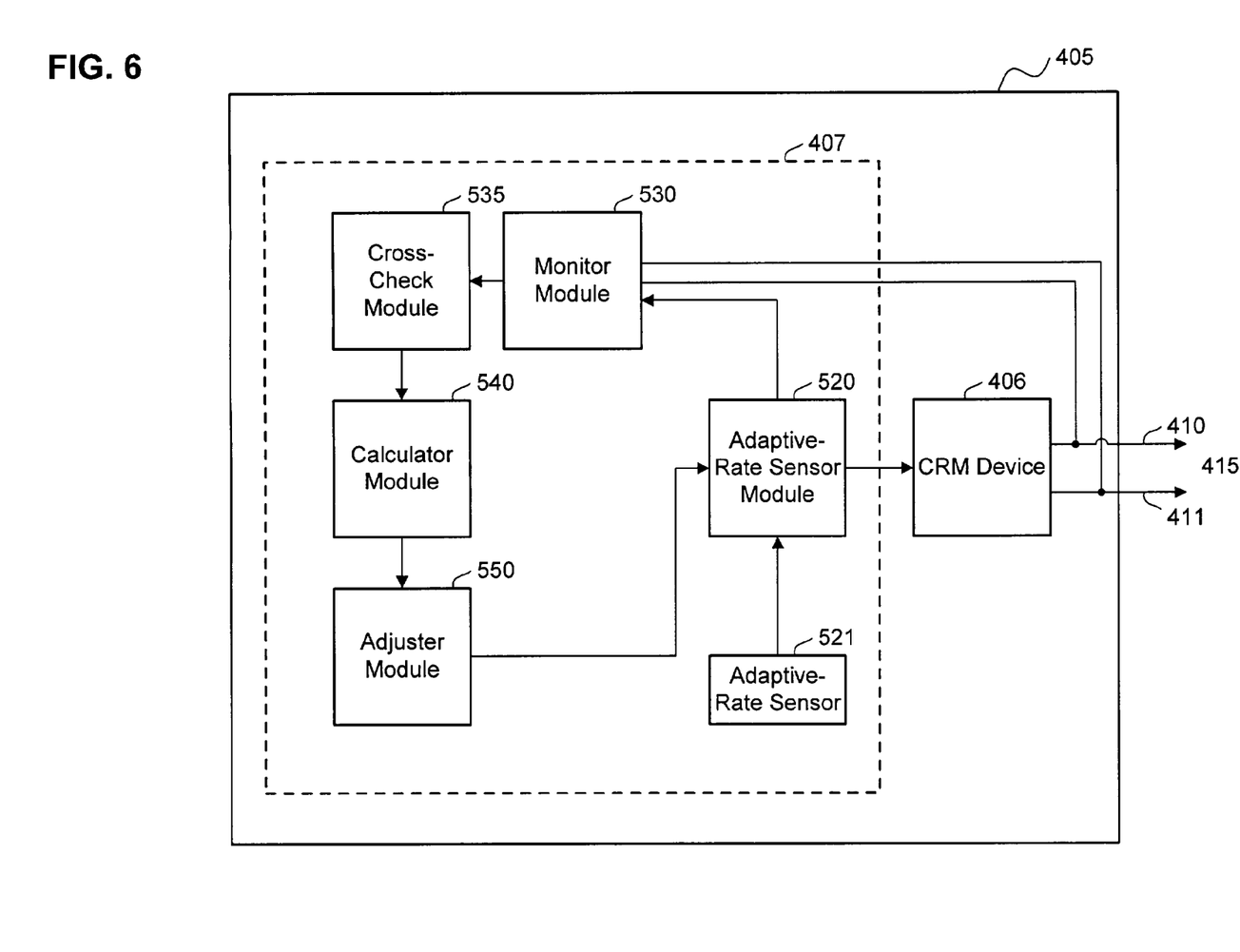
FIG. 6 depicts the cardiac rhythm management system of FIG. 5 with the adaptive-rate pacing device illustrated in greater detail.

The example CRM system 405 is also illustrated in FIG. 6, wherein the adaptive-rate pacing device 407 is shown in detail. The adaptive-rate pacing device 407 comprises an adaptive-rate sensor module 520, a monitor module 530, a cross-check module 535, a calculator module 540, and an adjuster module 550. The adaptive-rate sensor module 520 is coupled to the monitor module 530, the monitor module 530 is coupled to the cross-check module 535, the cross-check module 535 is coupled to the calculator module 540, the calculator module 540 is coupled to the adjuster module 550, and the adjuster module 550 is in turn coupled to the adaptive-rate sensor module 520. The monitor module 530 is further coupled to the heart 415 via the leads 410 and 411, or, alternatively, the monitor module 530 may be coupled to the heart 415 using separate leads.

The adaptive-rate sensor module 520 is coupled to the CRM device 406 and is further coupled to an adaptive-rate sensor 521. The adaptive-rate sensor 521 may take a variety of forms such as an activity, minute ventilation, QT interval sensor, or combination thereof, as described above. Other types of adaptive-rate sensors may also be used. The adaptive-rate sensor 521 measures an individual's activity or work load and communicates a signal proportional to the activity or work load to the adaptive-rate sensor module 520. The adaptive-rate sensor module 520 generally monitors the signals provided by the adaptive-rate sensor 521 and communicates with the CRM device 406 to increase pacing if the adaptive-rate sensor 521 measures an increase in activity. This increase in pacing will increase the individual's heart rate and associated cardiac output.

The monitor module 530 measures a heart rate of the individual. Specifically, the monitor module 530 monitors and records each daily maximum intrinsic heart rate (MIHR). The monitor module 530 further records the sensor response and/or sensor-indicated rate from the adaptive-rate sensor module 520 associated with each daily MIHR. The monitor module then passes each measured MIHR and associated sensor response and/or sensor-indicated rate to the cross-check module 535.

The cross-check module 535 verifies that each measured MIHR, as measured by the monitor module 630, is accurate and not a product of an arrhythmia or other abnormality. The cross-check module 535 accomplishes this by comparing each measured MIHR to the sensor response (the sensor-indicated rate can also be used) associated with the MIHR as provided by an adaptive-rate sensor module 520. If the sensor response is too low as compared to the MIHR, the measurement is dismissed as an abnormality (e.g., as would be the case in which an individual is at rest and experiencing tachycardia). Conversely, if the sensor response is commiserate with the MIHR, the cross-check module 635 will pass the MIHR and the associated sensor response to the calculator module 540. For some methods described below, cross-checking is not required, and therefore the module 535 may be removed.

The calculator module 540 performs a variety of calculations based on the data provided by the cross-check module 535. For example, the calculator module 540 may calculate an average maximum intrinsic heart rate $\overline{\text{MIHR}}$. The calculator module 540 may also compare values, such as the $\overline{\text{MIHR}}$, to other parameters associated with adaptive-rate pacing, such as a sensor rate target (SRT) and based on those comparisons, provide output to the adjuster module 550.

The output of the calculator module 540 is termed a calibrated parameter. The adjuster module 550 processes the calibrated parameter output from the calculator module 540 and may adjust one or more of the parameters associated with the adaptive-rate pacing device 407 based on the calibrated parameter. For example, the adjuster module 550 may adjust such parameters as the sensor rate target (SRT), the MSR, or a response factor (RF). The adjuster module 550 will then communicate any adjustments to the adaptive-rate sensor module 520.

The example CRM system 405, and specifically, the adaptive-rate pacing device 407 may implement various methods described below. These methods are similar in that each utilizes an individual's intrinsic chronotropic response to calibrate various adaptive-rate pacing parameters such as the SRT, MSR, or RF.

Figure 7:
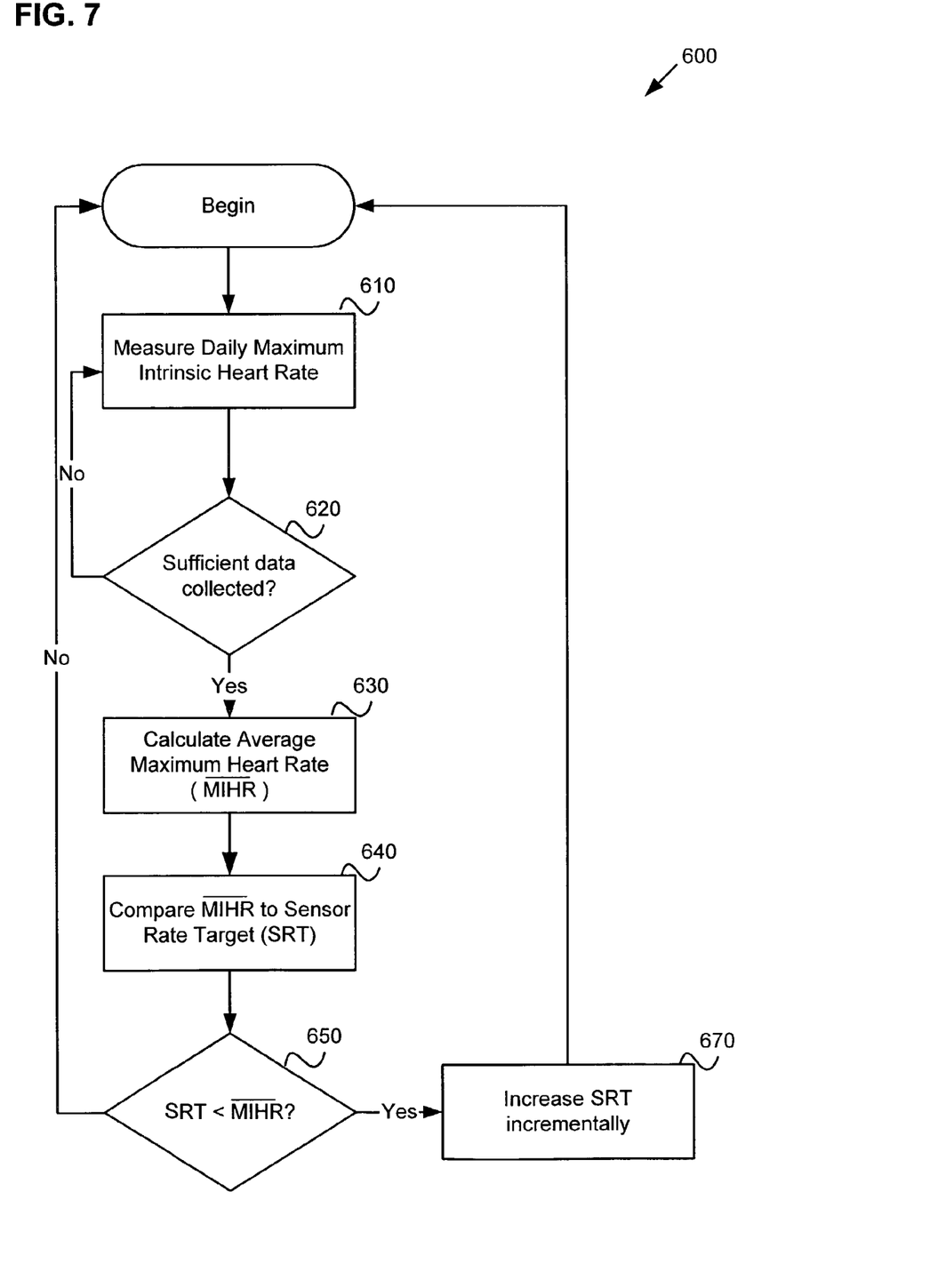
FIG. 7 shows a first example embodiment of an operational flow for calibrating a sensor rate target of a cardiac rhythm management system in accordance with the present invention.

II. Calibration of Sensor Rate Target Using Average Maximum Intrinsic Heart Rate A first example method 600 is shown in FIG. 7. The method 600 may be used to calibrate the SRT using the intrinsic chronotropic response. In operation 610, the daily maximum intrinsic heart rate (MIHR) is measured by, for example, the monitor module 530 of the adaptive-rate pacing device 407. Next, in operation 620, the device 407 determines whether a sufficient number of daily MIHRs have been recorded. In an example embodiment, a week's worth of daily MIHRs are recorded. However, other numbers, such as two weeks or a month, may also be used. If sufficient data has been collected, control is passed to operation 630. Otherwise, control is passed back to operation 610 for further monitoring.

In operation 630, the $\overline{\text{MIHR}}$ is calculated by, for example, the calculator module 540. Then, in operations 640 and 650, the $\overline{\text{MIHR}}$ is compared to the SRT for the adaptive-rate pacing device 407. If the $\overline{\text{MIHR}}$ is greater than the SRT, the SRT is increased incrementally in operation 670 by, for example, the adjuster module 550. Otherwise, if the $\overline{\text{MIHR}}$ is less than the SRT, the SRT is left unchanged. In this manner, the SRT may be calibrated using the individual's chronotropic response to increased activity.

III. Calibration of Response Factor Using Intrinsic Heart Rate

Figure 8:
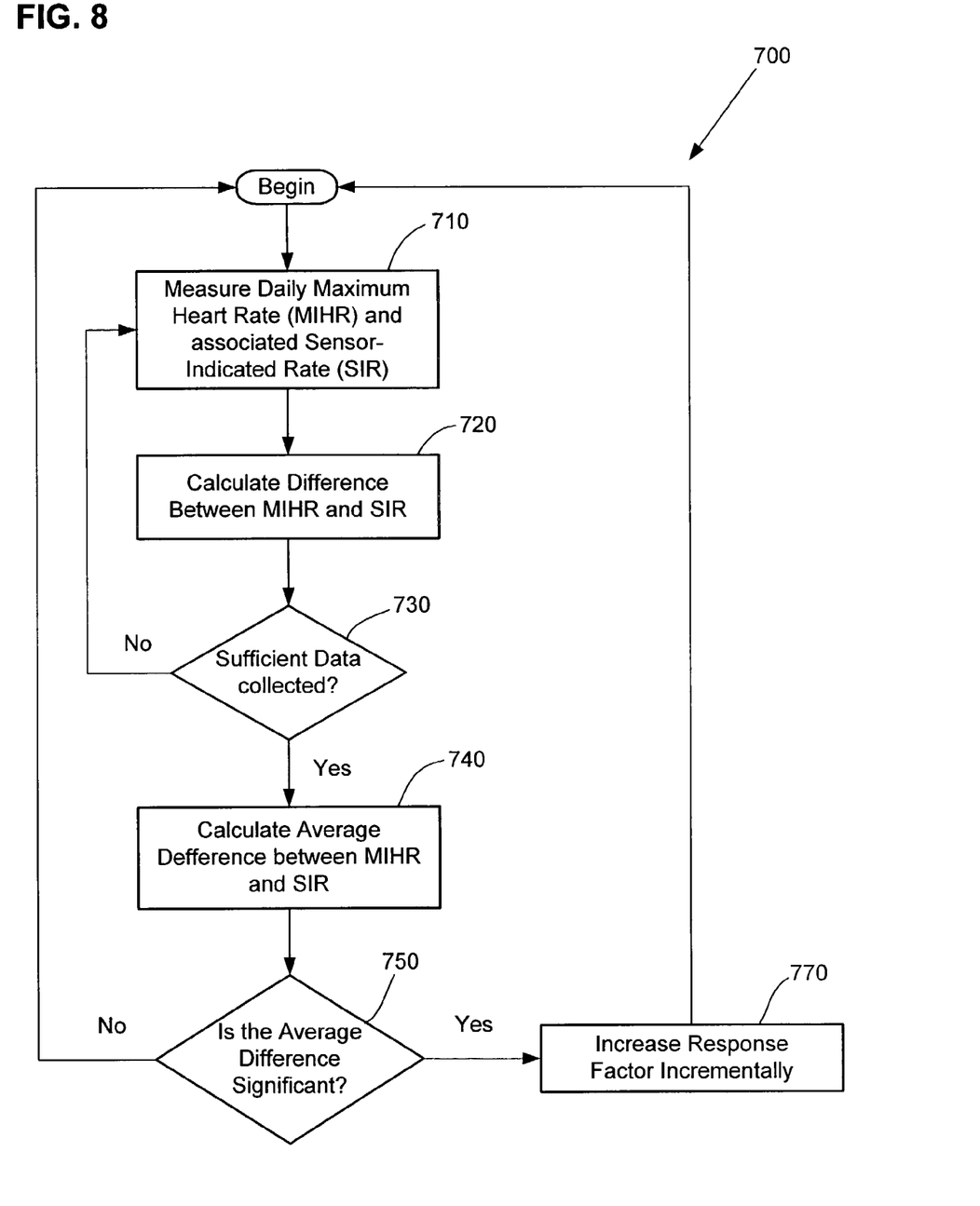
FIG. 8 shows a second example embodiment of an operational flow for calibrating a response factor of a cardiac rhythm management system in accordance with the present invention.

In a second example method 700 illustrated in FIG. 8, the RF may be calibrated using the maximum intrinsic heart rate (MIHR). In operation 710, the MIHR is measured by, for example, the monitor module 530. In addition, the sensor-indicated rate (SIR) from the adaptive-rate sensor module 520 associated with the MIHR is also recorded. This SIR provided by the adaptive-rate sensor module 520, although not used to pace the individual because the individual is chronotropic competent when the measurements are recorded, is still provided by the adaptive-rate sensor module 520 and may be recorded by the monitor module 530.

Then in operation 720, the difference between the MIHR and the SIR is calculated by, for example, the calculator module 540. Next, in operation 730, the device 407 determines whether a sufficient number of "differences" have been calculated. In the example embodiment, a week's worth of differences are used, but other numbers, such as two weeks or a month, may also be used. If sufficient data has been collected, control is passed to operation 740. Otherwise, control is passed back to operation 710.

Then, in operations 740 and 750, the average difference is calculated from all of the measured differences between each MIHR and associated SIR. If the average difference is significant, for example, the SIR provided by the adaptive-rate pacing device is consistently less than the chronotropic response, control is passed to operation 770 and the RF is increased incrementally. In the example embodiment, the response factor is increased incrementally by about 3%.

In the example embodiment, the average difference between the MIHR and the SIR is compared to a constant, and the RF is increased if the average difference is greater than the constant. In one example embodiment, the constant is set at 20 beats per minute, although other values may be used. As the RF factor is increased, the SIR increases to more closely approximate the individual's chronotropic response to activity. In this manner, the device 407 implementing the method 700 can automatically calibrate the SIR using the MIHR.

IV. Calibrate Maximum Sensor Rate Using Average Maximum Intrinsic Heart Rate

Figure 9:
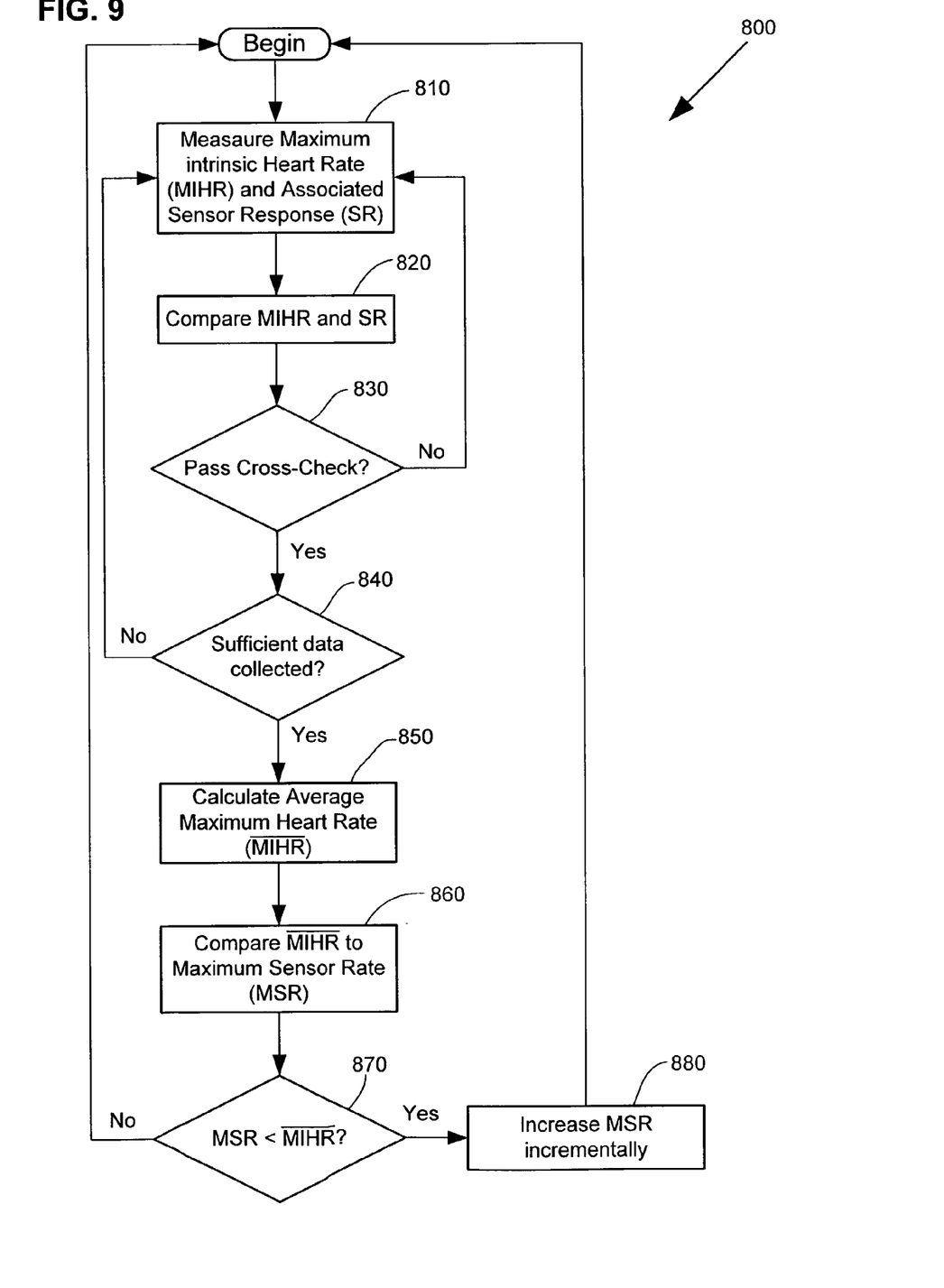
FIG. 9 shows a third example embodiment of an operational flow for calibrating a maximum sensor rate of a cardiac rhythm management system in accordance with the present invention.

A third method 800 is illustrated in FIG. 9, in which the maximum sensor rate (MSR) of the device 407 may be calibrated using the MIHR. In operation 810, the daily maximum intrinsic heart rate (MIHR) is measured by, for example, the monitor module 530. In addition, the sensor response from the adaptive-rate sensor module 520 associated with the daily MIHR is also recorded. Next, in operations 820 and 830, the daily MIHR is compared to the sensor response, and a cross-check by, for example, the module 535, is performed. The cross-check determines whether the sensor response, representing the activity of the individual as measured by the adaptive-rate sensor 521, is too low to be associated with the measured maximum heart rate. If the sensor response is determined to be too low with respect to the MIHR, the MIHR is discarded as abnormal (such as, for example, when an individual is experiencing an abnormally high heart rate due to tachycardia), and control is passed back to operation 810. Conversely, if the sensor response approximates an appropriate level for the MIHR, control is passed to operation 840.

In operation 840, the device 407 determines whether a sufficient number of MIHRs have been measured. In the example embodiment, a week's worth of MIHRs were used, but other numbers, such as two weeks or a month, may also be used. If sufficient data has been collected, control is passed to operation 850. Otherwise, control is passed back to operation 810. In operation 850, the module 540 calculates the average maximum intrinsic heart rate ($\overline{\text{MIHR}}$). Next, in operations 860 and 870, the MSR is compared to the calculated $\overline{\text{MIHR}}$. If the $\overline{\text{MIHR}}$ is consistently higher than the MSR, then the MSR is incrementally increased in operation 880. In one example embodiment, the MSR is incrementally increased by 5 beats per minute. However, other incremental increases may also be used. Otherwise, the method starts over again. In this manner, the MSR is calibrated using the individual's intrinsic chronotropic response to activity.

A CRM system, such as example CRM system 405, may implement one or more of the methods 600, 700, and 800 to calibrate parameters associated with adaptive-rate pacing based on an individual's intrinsic chronotropic response. In this manner, adaptive-rate pacing may more closely approximate an individual's intrinsic chronotropic response during periods of chronotropic incompetence.

A CRM system made according to the present invention and implementing one or more of the methods described above may be advantageous one or more reasons. A CRM system made in accordance with the present invention may automatically calibrate, using an individual's intrinsic chronotropic response, one or more parameters associated with adaptive-rate pacing, such as the sensor rate target, the response factor, and/or the maximum sensor rate. In this manner, adaptive-rate pacing may be optimized to approximate an intrinsic chronotropic response. Further, a CRM system made in accordance with the present invention may provide an accurate and fully-calibrated fall-back rate for individuals exhibiting atrial arrhythmias during which ventricular pacing is based solely on the adaptive-rate sensor-indicated rate. In addition, because monitoring of the heart rate is available in current CRM system functions, a CRM system made in accordance with the present invention would require minimal modification of current CRM system design. Other advantages may also become apparent through application of the present invention.

The systems and methods of the present disclosure can be implemented using a system as shown in the various figures disclosed herein comprising various devices and/or programmers, including implantable or external devices. Accordingly, the methods of the present disclosure can be implemented: (1) as a sequence of computer implemented steps running on the system; and (2) as interconnected modules within the system.

The implementation is a matter of choice dependent on the performance requirements of the system implementing the method of the present disclosure and the components selected by or utilized by the users of the method. Accordingly, the logical operations making up the embodiments of the method of the present disclosure described herein can be referred to variously as operations, steps, or modules. It will be recognized by one of ordinary skill in the art that the operations, steps, and modules may be implemented in software, in firmware, in special purpose digital logic, analog circuits, and any combination thereof without deviating from the spirit and scope of the present invention as recited within the claims attached hereto.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

What is claimed is:

1. An adaptive-rate pacing device, comprising:
   an adaptive-rate sensor module adapted to be coupled to a heart of an individual and an adaptive-rate sensor, wherein the adaptive-rate sensor is programmed to measure an activity level of the individual and communicate a signal proportional to the activity level to the adaptive-rate sensor module;
   a monitor module coupled to the adaptive-rate sensor module, wherein the monitor module is programmed to monitor a plurality of daily maximum intrinsic heart rates;
   a calculator module coupled to the monitor module, wherein the calculator module is programmed to calculates an average maximum intrinsic heart rate from the plurality of daily intrinsic maximum heart rates and compares the average maximum intrinsic heart rate to a maximum sensor rate of the adaptive-rate pacing device; and
   an adjuster module coupled to the calculator module, wherein the adjuster module is programmed to increases the maximum sensor rate if the average maximum intrinsic heart rate is greater than the maximum sensor rate.

2. The adaptive-rate pacing device of claim 1, wherein the calculator module is programmed to compares the average maximum intrinsic heart rate to a sensor rate target of the adaptive-rate pacing device, and wherein the adjuster module is programmed to increases the sensor rate target if the average maximum intrinsic heart rate is greater than the sensor rate target.

3. The adaptive-rate pacing device of claim 1, wherein the monitor module is programmed to monitors the plurality of daily maximum intrinsic heart rates and associated sensor-indicated rates, and wherein the calculator module is programmed to calculates a plurality of differences between each of the plurality of daily maximum intrinsic bean rates and associated sensor-indicated rates and calculates an average difference from the plurality of differences and compares the average difference to a constant, and wherein the adjuster module is programmed to increases a response factor of the adaptive-rate pacing device if the average difference is greater than the constant.

4. The adaptive-rate pacing device of claim 1, wherein the monitor module is further programmed to monitors a sensor response associated with each of the daily maximum intrinsic heart rates and cross-checks each of the plurality of daily maximum intrinsic heart rates with each associated sensor response.

5. A cardiac rhythm management system comprising:
   a cardiac rhythm management device adapted to be coupled to an individual's heart; and
   an adaptive-rate pacing device coupled to the cardiac rhythm management device, wherein the adaptive-rate pacing device is programmed to automatically calibrate at least one parameter of the adaptive-rate pacing device using an intrinsic chronotropic response of the individual, the adaptive-rate pacing device comprising:
      a monitor submodule programmed to register at least one daily maximum intrinsic heart rate over time, and to validate the at least one daily maximum intrinsic heart rate using sensor cross-checking;
      a calculator submodule coupled to the monitor module, wherein the calculator module is programmed to calculate a calibrated parameter based on the intrinsic chronotropic response; and
      an adjuster submodule coupled to the calculator module, wherein the adjuster module is programmed to adjust the adaptive-rate pacing device based on the calibrated parameter, wherein the calibrated parameter is a maximum sensor rate of the adaptive-rate pacing device.

6. A method for automatically calibrating adaptive-rate pacing provided by a cardiac rhythm management system, the method comprising:

monitoring a plurality of daily maximum intrinsic heart rates and associated sensor response;

cross-checking each of the plurality of daily maximum intrinsic heart rates by comparing each of the plurality of daily maximum intrinsic heart rates to each associated sensor response;

calculating an average maximum intrinsic heart rate from the plurality of daily maximum intrinsic heart rates;

comparing the average maximum intrinsic heart rate to a maximum sensor rate; and increasing the maximum sensor rate if the avenge maximum intrinsic heart rate is greater than the maximum sensor rate.

* * * * *

UNITED STATES PATENT AND TRADEMARK OFFICE
CERTIFICATE OF CORRECTION

PATENT NO. : 7,050,854 B2  
APPLICATION NO. : 10/178277  
DATED : May 23, 2006  
INVENTOR(S) : Daum et al.

Page 1 of 2

It is certified that error appears in the above-identified patent and that said Letters Patent is hereby corrected as shown below:

On the Title page, item (56), under "Other Publications", in column 2, line 4, delete "Balckburn," and insert -- Blackburn, --, therefor.

In column 12, lines 6-7, in Claim 1, delete "calculates" and insert -- calculate --, therefor.

In column 12, line 14, in Claim 1, delete "increases" and insert -- increase --, therefor.

In column 12, line 18, in Claim 2, delete "compares" and insert -- compare --, therefor.

In column 12, line 21, in Claim 2, delete "increases" and insert -- increase --, therefor.

In column 12, line 25, in Claim 3, delete "monitors" and insert -- monitor --, therefor.

In column 12, line 28, in Claim 3, delete "calculates" and insert -- calculate --, therefor.

In column 12, line 29, in Claim 3, delete "bean" and insert -- heart --, therefor.

In column 12, line 33, in Claim 3, delete "increases" and insert -- increase --, therefor.

In column 12, line 37, in Claim 4, delete "monitors" and insert -- monitor --, therefor.

In column 12, line 39, in Claim 4, delete "cross-checks" and insert -- cross-check --, therefor.

UNITED STATES PATENT AND TRADEMARK OFFICE
CERTIFICATE OF CORRECTION

PATENT NO. : 7,050,854 B2
APPLICATION NO. : 10/178277
DATED : May 23, 2006
INVENTOR(S) : Daum et al.

It is certified that error appears in the above-identified patent and that said Letters Patent is hereby corrected as shown below:

In column 14, line 3, in Claim 6, delete "avenge" and insert -- average --, therefor.

Signed and Sealed this

Nineteenth Day of December, 2006

JON W. DUDAS
*Director of the United States Patent and Trademark Office*